US011860153B2

(12) United States Patent
Januel (10) Patent No.: US 11,860,153 B2
(45) Date of Patent: Jan. 2, 2024

(54) DEVICE FOR STORING AND DISPENSING STRIPS

(71) Applicant: BIOMÉRIEUX, Marcy l'Etoile (FR)

(72) Inventor: Denis Januel, Amberieu en Bugey (FR)

(73) Assignee: BIOMÉRIEUX, Marcy-l'Etoile (FR)

( * ) Notice: Subject to any disclaimer, the term of this patent is extended or adjusted under 35 U.S.C. 154(b) by 0 days.

(21) Appl. No.: 17/782,052

(22) PCT Filed: Dec. 15, 2020

(86) PCT No.: PCT/FR2020/000274
§ 371 (c)(1),
(2) Date: Jun. 2, 2022

(87) PCT Pub. No.: WO2021/123516
PCT Pub. Date: Jun. 24, 2021

(65) Prior Publication Data
US 2023/0003712 A1    Jan. 5, 2023

(30) Foreign Application Priority Data
Dec. 16, 2019   (FR) ........................................ 1914454

(51) Int. Cl.
*B67D 1/00*   (2006.01)
*B65G 17/32*   (2006.01)
(Continued)

(52) U.S. Cl.
CPC ....... *G01N 33/48778* (2013.01); *B21C 49/00* (2013.01); *B65D 83/08* (2013.01)

(58) Field of Classification Search
CPC .... B21C 49/00; B65D 83/08; B65D 83/0852; B65H 3/02; B65H 37/005; G01N 33/48757; G01N 33/48778
See application file for complete search history.

(56) References Cited

U.S. PATENT DOCUMENTS 2,981,408 A * 4/1961 Gamble ................. B65H 35/06
                                                 206/559
3,664,546 A * 5/1972 Shelly ...................... A47F 1/06
                                                 221/311
(Continued)

FOREIGN PATENT DOCUMENTS

DE    20 2009 010 651 U1    10/2009
WO    2014/134455 A1    9/2014

OTHER PUBLICATIONS

Apr. 26, 2021 Written Opinion of the International Searching Authority for International Application No. PCT/FR2020/000274.

*Primary Examiner* — Gene O Crawford
*Assistant Examiner* — Kelvin L Randall, Jr.
(74) *Attorney, Agent, or Firm* — Oliff PLC (57) ABSTRACT

A device for storing and dispensing strips, including at least one cartridge which includes a recess including a first portion with a base shaped to receive at least one strip, the storage device further including at least one dispensing member including a projection with a contact surface shaped to cover at least a first end of each strip, wherein the dispensing member is at least partially housed in a second portion of the cartridge recess, the first portion of the recess and the second portion of the recess are connected by an angled intermediate portion and the dispensing member is configured to be rotatable between a rest position in which the projection extends away from the angled intermediate portion and an operating position in which the projection converges with the angled intermediate portion so as to at least press the first end of each strip against the angled intermediate portion.

11 Claims, 4 Drawing Sheets

(51) Int. Cl.
  *B65G 47/22* (2006.01)
  *B65G 47/44* (2006.01)
  *G01N 33/487* (2006.01)
  *B21C 49/00* (2006.01)
  *B65D 83/08* (2006.01)

(56) References Cited

U.S. PATENT DOCUMENTS

| | | | | |
|---|---|---|---|---|
| 3,767,082 | A * | 10/1973 | House | B65G 1/07 |
| | | | | 221/312 R |
| 4,753,369 | A * | 6/1988 | Morrison | A47K 10/42 |
| | | | | 221/56 |
| 5,193,795 | A * | 3/1993 | Ackeret | B65H 3/46 |
| | | | | 40/511 |
| 9,033,184 | B2 * | 5/2015 | Walter | B65D 83/10 |
| | | | | 221/256 |
| 2009/0302048 | A1 * | 12/2009 | Nobilet | B65D 83/087 |
| | | | | 221/259 |
| 2016/0223515 | A1 * | 8/2016 | Bilton | G01N 33/66 |
| 2017/0253420 | A1 | 9/2017 | Smith | |

* cited by examiner

DEVICE FOR STORING AND DISPENSING STRIPS

TECHNICAL FIELD OF THE INVENTION

The invention concerns the technical field of biological analysis. More particularly, the invention relates to devices containing analysis strips.

In the field of biological analysis, strips referred to as analysis strips may be used, which make it possible to determine the concentration of one or more analytes in biological fluids or to detect low resistance levels, confirm or detect a specific resistance phenotype, or alternatively confirm an antibiogram result. These strips may be "MIC" strips for determining the minimum inhibitory concentration of an antibiotic, an antifungal or an antitubercular, which are marketed in particular under the brand ETEST® by the company bioMérieux.

In order to preserve their integrity, these strips must be maintained at a certain level of humidity and must remain free of foreign substances. Thus, in order to avoid any contamination, these strips must not be handled before their use and they must be kept in hermetic containers until use.

Document WO2012069758 discloses the use of individually packaged single-use sterile analysis strips. Specifically, this document describes a breakable package into which an analysis strip and a desiccating means are inserted, the desiccating means also constituting a means for perforating the package in order to access the strip.

This type of device has the minor drawback that it can contain only a single strip when an analysis requires the use of a plurality of strips.

OBJECT OF THE INVENTION

The object of the invention is to improve the device described above that is intended in particular to contain, protect and improve the gripping of strips when the latter are stored together in the same container.

For this purpose, the invention relates to a device for storing and dispensing strips, comprising at least one cartridge comprising a cavity with a bottom, at least a first portion of the cavity being shaped in order to receive at least one strip and preferably a plurality of strips,
characterized in that the storage device furthermore comprises at least one dispensing member configured in order to cooperate with the cartridge, said dispensing member being at least partially accommodated in a second portion of the cavity of the cartridge, the first portion of the cavity and the second portion of the cavity being connected by an inclined intermediate portion, the second portion of the cavity being deeper than the first portion with respect to an axis substantially perpendicular to the bottom of the cavity,
and in that the dispensing member comprises a protruding part having a contact surface shaped in order to cover at least a first end of each strip, the contact surface facing toward the bottom of the cavity of the cartridge and overhanging the inclined intermediate portion, said dispensing member being configured at least to be mobile in rotation between:
a resting position, in which the protruding part extends at a distance from the inclined intermediate portion,
an operating position, in which the protruding part converges toward the intermediate portion so as at least to press the first end of each strip against the inclined intermediate portion.

The device according to the invention makes it possible to contain a plurality of strips and to facilitate gripping of the strips. Specifically, in the operating position, the dispensing member converges toward the inclined intermediate portion so that at least the first end of each strip covered by the contact surface of the protruding part of the dispensing member is pressed against the inclined intermediate portion and is preferably pinched between the protruding part and the inclined intermediate portion. The pressing/pinching of the first end of each strip leads to tilting of these strips, arranging them in a fantail in order to allow individual gripping of each one.

According to one characteristic of the invention, the dispensing member is a desiccating member, which makes it possible to ensure protection of all the strips against humidity throughout its lifetime, and to do so irrespective of the number of strips inside the storage device. Thus, according to one characteristic of the invention, the dispensing member is composed of plastic and a desiccating material.

According to one characteristic of the invention, the dispensing member passes from the resting position to the operating position by the exertion of a pressure on the protruding part of the dispensing member. Preferably, the pressure is exerted at the level of the protruding part of the dispensing member. This pressure makes it possible to raise the strips and recover them with a manual gripping instrument.

According to one characteristic of the invention, the dispensing member is permanently accommodated in the cartridge.

According to one characteristic of the invention, the cartridge has a substantially rectangular shape.

According to one characteristic of the invention, the cavity of the cartridge is longitudinal, preferably centered in the cartridge. Advantageously, the cavity of the cartridge is shaped in order to accommodate the strips tightly. Thus, the strips remain in position and are prevented from moving horizontally.

According to one characteristic of the invention, the part of the bottom of the cavity at the level of the second portion is offset downward along the axis D-D substantially perpendicular to the bottom.

Advantageously, the inclined intermediate portion has a slope of between 25° and 35°.

According to the invention, the cartridge may comprise lateral indentations which are formed on either side of the cartridge and are configured in order to allow it to be held in position in the tool for picking up the strips.

Furthermore, according to one characteristic of the invention, the cartridge comprises at least one retaining tab positioned at one end of the cavity of the cartridge. Preferably,
the retaining tab is formed on the first portion of the cavity.

According to the invention, the retaining tab is configured in order to prevent accidental removal of a plurality of strips at the same time from the cavity, in particular when the storage device is being used in an automatic machine.

According to one characteristic of the invention, the storage device comprises a sealing capsule applied, preferably welded, onto the cartridge. The capsule allows the cartridge to be rendered leaktight before first use. Advantageously, the sealing capsule is preferably made of aluminum.

According to one characteristic of the invention, the device comprises a cover intended to cooperate with the cartridge. Advantageously, the cover is used to provide leaktight protection once the sealing capsule has been opened.

According to one characteristic of the invention, the cover has a circumferential edge intended to cooperate with the cartridge by shape complementarity and preferably by clipping.

According to one characteristic of the invention, the cover comprises an internal face intended to face toward the cartridge, said internal face comprising at least one retaining rib extending longitudinally over said internal face and being intended to be arranged at least partially in the cavity, and preferably the first portion of the cavity of the cartridge, when the cover cooperates with the cartridge. Advantageously, the retaining rib or ribs make it possible to keep the strips in the cavity of the cartridge and therefore to prevent them from moving or turning over during transport of the storage device.

According to one characteristic of the invention, the cover comprises at least one joint overmolded or bi-injected on the internal face of the cover in order to improve the leaktightness.

According to one characteristic of the invention, the joint is shaped in order to cooperate with the shape of the cavity. Advantageously, the joint is in the form of an elongate ring or a bead in the shape of a ring.

According to one characteristic of the invention, the cover comprises a poka-yoke intended to indicate the closure direction. Advantageously, the poka-yoke is arranged at the level of a closure member of the cartridge.

Advantageously, the shape of the dispensing member is optimized in order to allow mechanical operation thereof while maintaining a maximum humidity absorption capacity.

According to one characteristic of the invention, the dispensing member comprises a second part which is widened with respect to the protruding part, in order to ensure its position in the cartridge and increase its volume, and therefore its desiccating power.

According to one characteristic of the invention, the protruding part extends radially with respect to the second part.

According to one characteristic of the invention, the dispensing member is recessed so as to optimize the molding of said member and also to optimize the absorption surface area.

According to one characteristic of the invention, the dispensing member has a front-to-rear cross section of substantially triangular shape along the longitudinal axis. This shape makes it possible to promote tilting of the dispensing member forward, that is to say toward the protruding part.

According to one characteristic of the invention, each strip comprises a first end intended to be retained by the protruding part of the dispensing member.

Moreover, according to one characteristic of the invention, each strip comprises a second end, opposite the first end, intended to be retained by a retaining tab.

Advantageously, the strip or strips are analysis strips making it possible to determine the concentration of one or more analytes in biological fluids or to detect low resistance levels, confirm or detect a specific resistance phenotype, or alternatively confirm an antibiogram result. These strips may be "MIC" strips for determining the minimum inhibitory concentration of an antibiotic, an antifungal or an antitubercular, which are marketed in particular under the brand ETEST® by the company bioMérieux.

According to one characteristic of the invention, the cover furthermore comprises at least one transverse holding rib arranged on the internal face of the cover, facing toward the cavity, and configured in order to make it possible to hold the strips inside the cavity when the cover is positioned on the cartridge.

The invention also relates to an assembly comprising at least one analysis strip, preferably a plurality of analysis strips, and a storage device, the at least one analysis strip being accommodated in the first part of the cavity of the storage device, positioned flat with respect to the bottom of the cavity, along the longitudinal axis of the device.

According to one characteristic of the invention, in the resting position of the dispensing member, the first end of each strip rests under the contact surface of the protruding part of the dispensing member.

According to one characteristic of the invention, in the operating position of the dispensing member, the first end of each strip is pinched between the protruding part of the dispensing member and the inclined intermediate portion.

In the present invention, a dispensing member is intended to mean a member produced at least partly from a material containing a molecular sieve or a chemical agent making it possible to absorb water/humidity.

BRIEF DESCRIPTION OF THE FIGURES

The invention will be understood more clearly from the following description, which relates to an embodiment according to the present invention given by way of nonlimiting example and explained with reference to the appended schematic figures. The appended schematic figures are listed below.

DETAILED DESCRIPTION

In the example illustrated in the figures, the storage device 1 according to the invention comprises a cartridge 10, which is covered with a cover 11, and a dispensing member 12. This storage device forms part of an assembly furthermore comprising a plurality of strips 13 intended to be accommodated in the cartridge 10 of the device 1.

Figure 1:
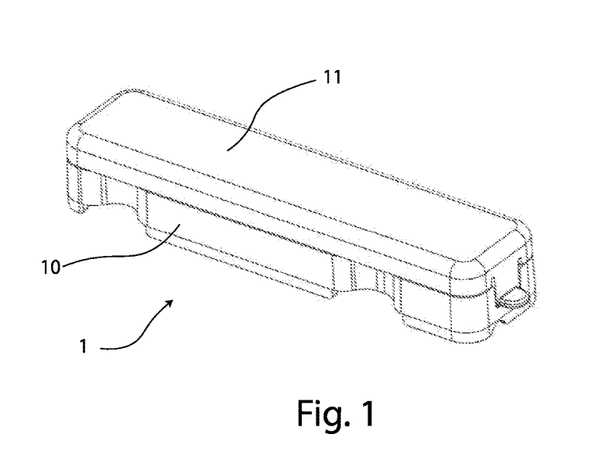
FIG. 1 is a perspective view of the hermetically closed assembly according to the invention.
Figure 2:
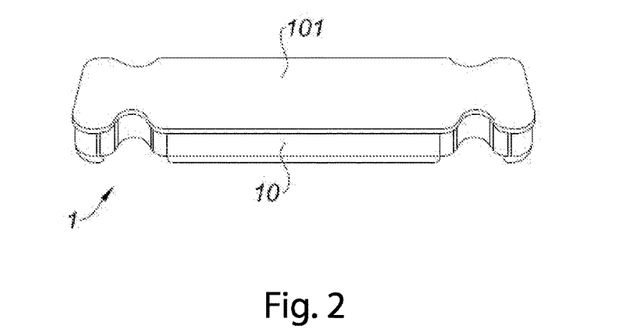
FIG. 2 is a perspective view of the hermetically closed assembly without a cover.

FIG. 1 illustrates the closed storage device 1. In FIG. 2, the assembly 1 is open and the cover 11 has been removed. This figure therefore shows the cartridge 10 covered with a capsule 101 making it possible to maintain the leaktightness of the cartridge even though the cover 11 has been removed. The capsule 101 covers the entirety of the upper face of the cartridge 10.

Figure 3:
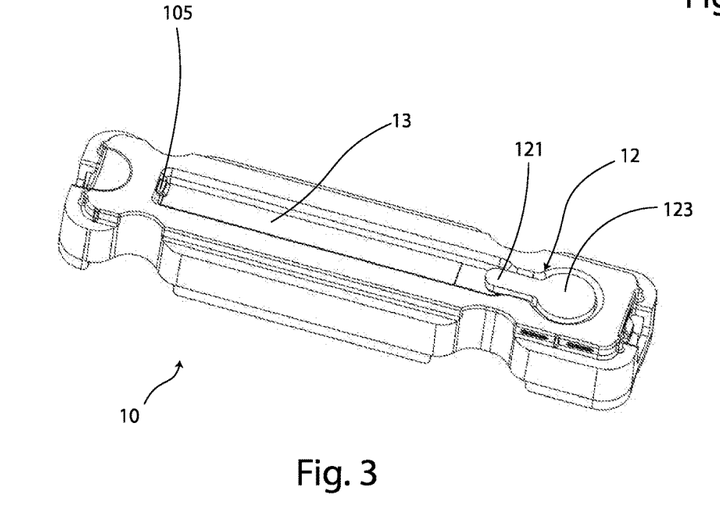
FIG. 3 is a perspective view of the open assembly.

Opening the capsule 101, as illustrated in FIG. 3, uncovers the cartridge 10 comprising a cavity 102, in which a plurality of analysis strips 13 are accommodated, and a dispensing member 12.

Figure 4:
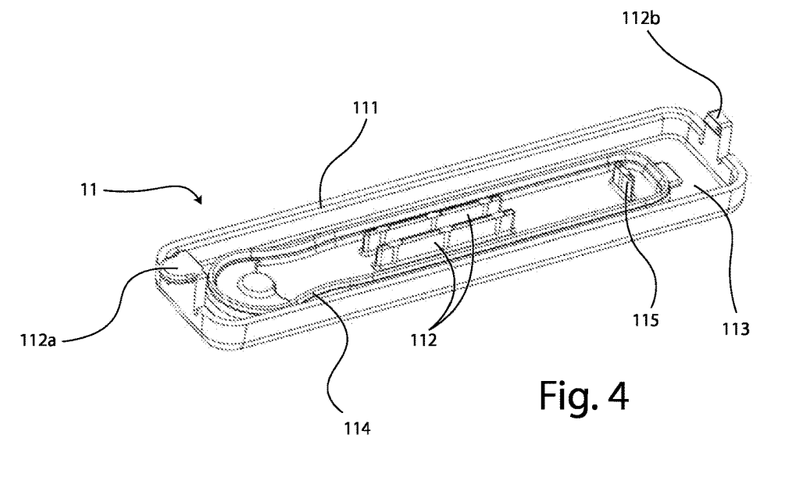
FIG. 4 is a perspective view of the cover, viewed from below.

The cover 11 of the assembly 1 is illustrated in more detail in FIG. 4. The cover has a circumferential edge 111 intended to cooperate with the cartridge 10 by shape complementarity and preferably by clipping. More particularly, the cover comprises a first tongue 112a at one end, intended to cooperate with a first engagement orifice 104a formed on the cartridge 10, and a second tongue 112b positioned at the opposite end and intended to cooperate with a second engagement orifice 104b formed on the cartridge 10.

Advantageously, the fact that the first engagement orifice 104a and the second engagement orifice 104b are not identical is referred to as a poka-yoke. Specifically, each has an opening with a different size, so that the cover 11 can be engaged on the cartridge 10 in only one direction respectively via the first tongue 112a and the second tongue 112b. For these purposes, the first tongue 112a of the cover 11 can cooperate only with the first engagement orifice 104a and the second tongue 112b of the cover 11 can engage only with the second engagement orifice 104b.

Furthermore, the cover 11 comprises a face 113 intended to face toward the cartridge 10, said internal face 113 comprising two ribs 112 extending longitudinally on said internal face 113. The two ribs 112 are arranged parallel to one another and preferably substantially in the middle of the internal face 113 of the cover 11. The two ribs 112 are positioned so as to be able to hold the strips 13 in the cavity 102 of the cartridge 10 when the cover 11 covers the cartridge 10. In a variant which is not represented, the internal face 113 has a single rib 112 arranged transversely and substantially in the middle of said internal face 113.

Moreover, the cover 11 comprises a joint 114 having a shape substantially complementary with a longitudinal cavity 102 which is formed in the cartridge 10 and is configured in order to accommodate the strips 13. Advantageously, the joint 114 is fitted on the internal face 113 of the cover 11, as may be seen in FIG. 4.

Furthermore, as may be seen particularly in FIG. 4, the cover 11 furthermore comprises at least one transverse holding rib 115 which is arranged on the internal face of the cover 11, facing toward the longitudinal cavity 12, and is configured in order to make it possible to hold the strips inside the cavity when the cover 11 is positioned on the cartridge 10.

The cartridge 10 according to the invention has a substantially rectangular shape. The cartridge 10 comprises a longitudinal cavity 102 which is preferably centered, as may be seen particularly in FIG. 5. The cavity 102 comprises a bottom 103. Furthermore, the cavity 102 comprises a first portion 102a shaped in order to receive at least one strip 13 and preferably a plurality of strips 13, and a second portion 102b shaped in order to at least partly accommodate the dispensing member 12, as illustrated in FIG. 6.

Figure 6:
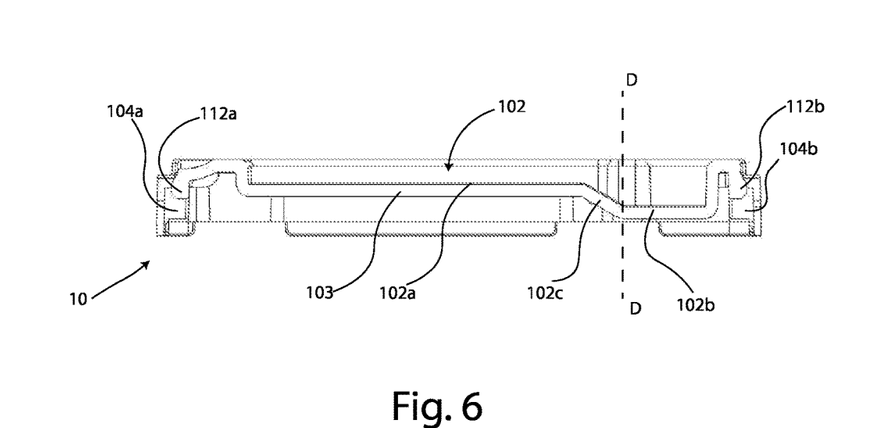
FIG. 6 is a view in longitudinal section of the cartridge represented in FIG. 5, along the axis A-A.

In the example illustrated in FIG. 6, the first portion 102a of the cavity and the second portion 102b of the cavity 102 are connected by an inclined intermediate portion 102c, the second portion 102b of the cavity 102 being deeper than the first portion 102a with respect to an axis D-D substantially perpendicular to the bottom 103 of the cavity 102. In other words, the part of the bottom 103 of the cavity 102 at the level of the second portion 102b is offset downward, that is to say away from the upper face of the cartridge 10, along the axis D-D substantially perpendicular to the bottom 103.

Advantageously, the inclined intermediate portion has a slope of between 25° and 35°.

Figure 5:
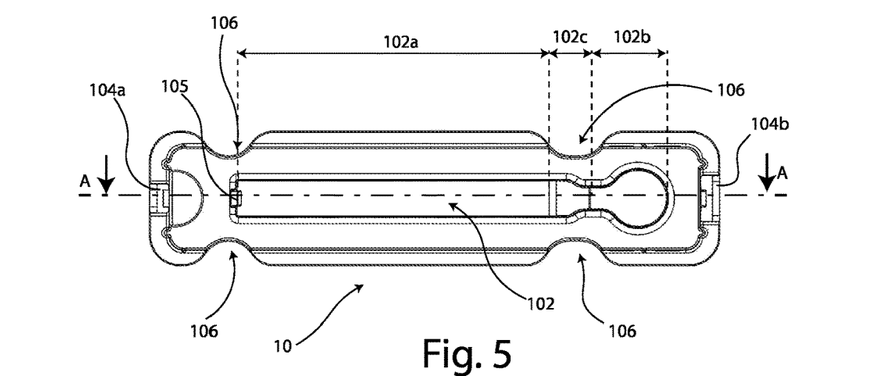
FIG. 5 is a view from above of the cartridge according to the invention.

Moreover, as may be seen particularly in FIG. 5, the cartridge 10 comprises a first engagement orifice 104a formed on a first end of the cartridge and intended to cooperate with the first tongue 112a of the cover 11. The cartridge 10 also comprises a second engagement orifice 104b on a second end of the cartridge, opposite the first end, which is intended to cooperate with the second tongue 112b of the cover 11.

According to the invention, the cartridge 10 may comprise lateral indentations 106 which are formed symmetrically on either side of the cartridge and are configured in order to allow it to be held in position in the tool for picking up the strips.

Furthermore, the cartridge 10 comprises at least one retaining tab 105 positioned at one end of the cavity 102 of the cartridge 10. The retaining tab 105 is formed on the first portion 102a of the cavity 102. The retaining tab 105 is configured in order to prevent the strips from leaving the cavity 102. The retaining tab 105 also makes it possible to facilitate gripping at the middle of the strip by an instrument, as may be seen in FIG. 13. The retaining tab 105 holds the second end 132 of the strips 13.

Figure 7:
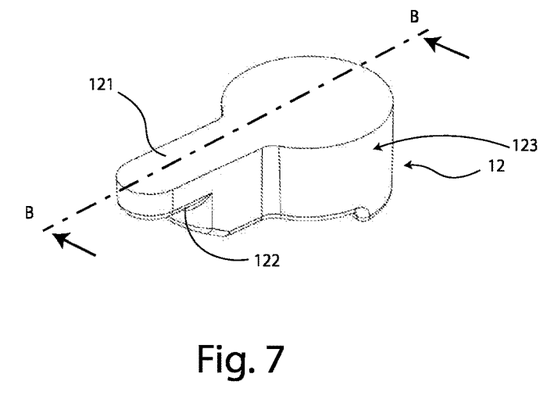
FIG. 7 is a perspective view from above of the dispensing member.
Figure 8:
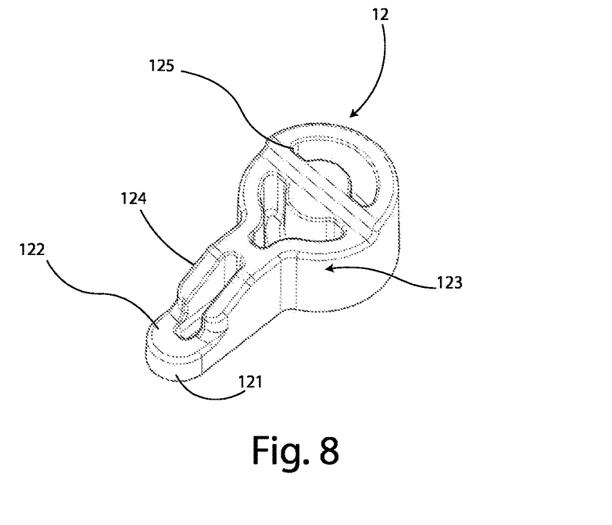
FIG. 8 is a perspective view from below of the dispensing member.
Figure 9:
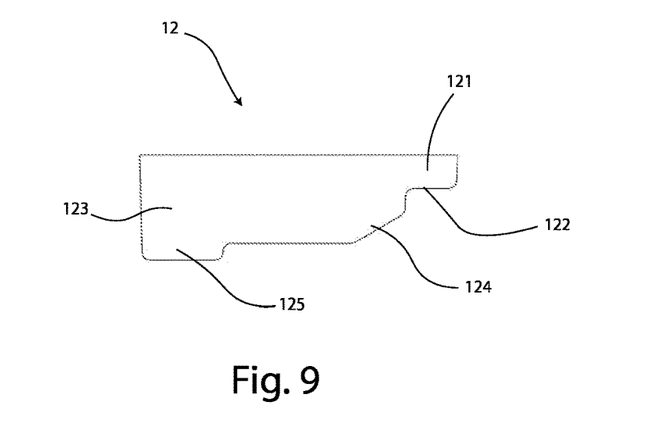
FIG. 9 is a view in front-to-rear cross section along an axis B-B of the dispensing member represented in FIGS. 7 and 8.

The dispensing member 12 is illustrated particularly in FIGS. 7 to 9. The dispensing member is configured in order to cooperate with the cartridge 10, said dispensing member 12 being at least partially accommodated in a second portion 102b of the cavity 102 of the cartridge 10, as illustrated particularly in FIGS. 10 and 11.

As may be seen in FIGS. 7 and 8, the dispensing member 12 comprises a protruding part 121 having a contact surface 122 shaped in order to cover at least a first end 131 of each strip 13, the contact surface 122 facing toward the bottom 103 of the cavity 102 of the cartridge 10 and overhanging the inclined intermediate portion 102c.

Furthermore, the dispensing member 12 comprises a second part 123 which is widened with respect to the protruding part 121. More particularly, the protruding part 121 extends radially or laterally (depending on the shape of the second part) with respect to the second part 123.

Furthermore, the dispensing member has a front-to-rear cross section of substantially triangular shape along the longitudinal axis, as illustrated in FIG. 9. This shape makes it possible to promote tilting of the dispensing member 12 forward, that is to say toward the protruding part 121. Specifically, as may be seen in FIGS. 8 and 9, the second part 123 of the dispensing member 12 has a bearing surface 125 followed by a shoulder, followed by a plane surface substantially parallel to the bearing surface 125. An inclined portion 124 connects the plane surface to the protruding part 121 of the dispensing member 12.

Figure 10:
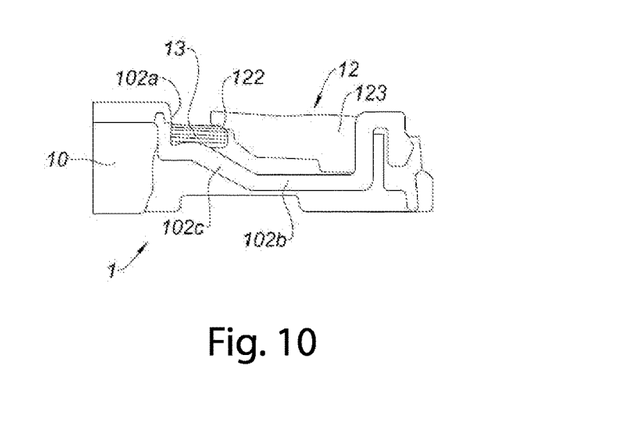
FIG. 10 is a view in longitudinal section of the device according to the invention, the dispensing member being in the resting position.
Figure 11:
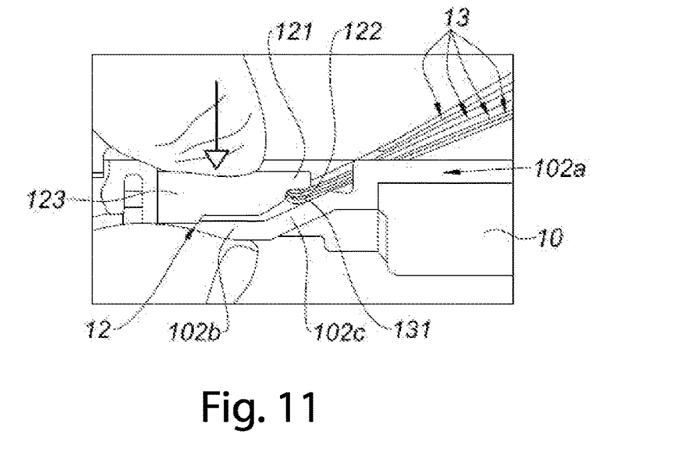
FIG. 11 is a view in longitudinal section of the device according to the invention, the dispensing member being in the operating position.
Figure 12:
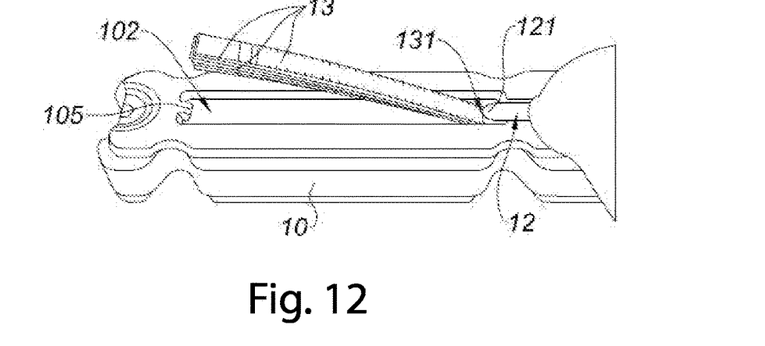
FIG. 12 is a perspective view of the device according to the invention, the dispensing member being in the operating position.
Figure 13:
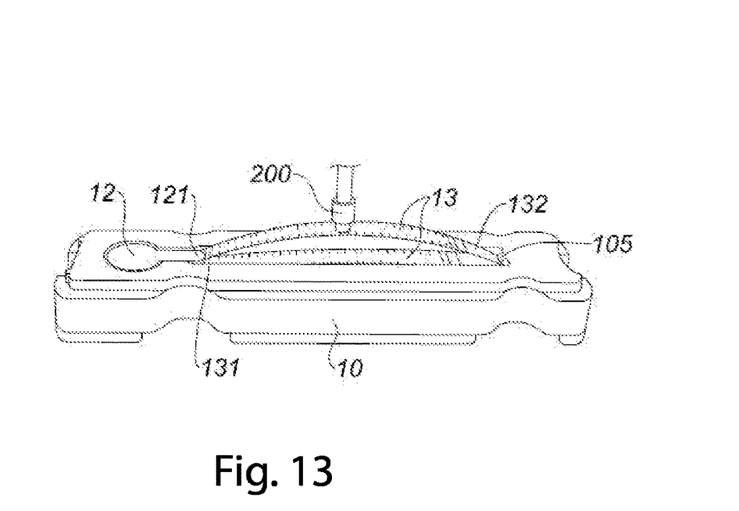
FIG. 13 is a perspective view of the device according to the invention, a gripping instrument being put in place in order to grip a strip.

The object of the invention is, in particular, to facilitate individual gripping of the strips stored together in the same container. For this purpose, the dispensing member 12 is configured in order to be mobile in rotation between:

a resting position illustrated in FIG. 10, in which the protruding part 121 extends at a distance from the inclined intermediate portion 102c, and an operating position illustrated in FIGS. 11, 12, 13, in which the protruding part 121 converges toward the inclined intermediate portion 102c so that the first end 131 of each strip 13 is at least pressed against the inclined intermediate portion 102c, and is preferably pinched between the protruding part 121 and the inclined intermediate portion 102c.

As may be seen in FIG. 10, the strips 13 are covered on a first end 131 by the protruding part 121 of the dispensing member 12. During the tilting/rotation of the dispensing member 12, in the operating position, the protruding part 121 bears on the end 131 of the strips against the inclined intermediate portion 102c of the cartridge, thereby causing tilting of the strips as illustrated in FIG. 12. When the pressure exerted on the dispensing member is manually released, the retaining tab 105 is no longer capable of retaining the second end 132 of the strips 13, which thus allows individual manual gripping of said strips 13.

Moreover, when the pressure exerted on the dispensing member is less strong than a standard manual pressure, the retaining tab 105 retains the second end 132 of the strips 13, causing the strips 13 to curve as illustrated in FIG. 13, which allows gripping by an instrument 200 of the automatic type, for example by suction of the center of the strip 13. Furthermore, this curvature makes it possible to create a friction movement between the gripped strip and the strip located directly below, which could be adhesively bonded, and to separate them.

In both cases, the full tilting or curvature of the strips allows detachment of the strips from one another and makes it possible to grip a single strip at a time, irrespective of the instrument used. This furthermore makes it possible to ensure that the strip located below remains in place in the cartridge and does not turn over.

In FIG. 12, a manual instrument or the hand of an operator may be used, while in FIG. 13 an automatic instrument (suction cup or any other gripping system) may be used.

Of course, the invention is not limited to the embodiments described and represented in the appended figures. Modifications remain possible, particularly in terms of the construction of the various elements or by substitution of technical equivalents, without thereby departing from the protective scope of the invention.

The invention claimed is:

1. A storage device for storing and dispensing strips, the storage device comprising:
   a cartridge comprising a cavity, the cavity comprising:
      a bottom;
      a first portion shaped in order to receive strips;
      a second portion that is deeper than the first portion with respect to an axis D-D substantially perpendicular to the bottom of the cavity; and
      an inclined intermediate portion connecting the first portion and the second portion;
   a dispensing member configured to cooperate with the cartridge, the dispensing member being at least partially accommodated in the second portion, the dispensing member comprising:
      a protruding part having a contact surface shaped in order to cover at least a first end of each of the strips, the contact surface facing toward the bottom of the cavity of the cartridge and overhanging the inclined intermediate portion,
   wherein the dispensing member is configured to be mobile in rotation between:
      a resting position, in which the protruding part extends at a distance from the inclined intermediate portion, and
      an operating position, in which the protruding part converges toward the inclined intermediate portion so as to press the first end of each of the strips against the inclined intermediate portion.

2. The storage device as claimed in claim 1, wherein the dispensing member is a desiccating member.

3. The storage device as claimed in claim 1, wherein the inclined intermediate portion has a slope of between 25° and 35°.

4. The storage device as claimed in claim 1, wherein the cartridge comprises at least one retaining tab positioned at one end of the cavity of the cartridge.

5. The storage device as claimed in claim 1, wherein the dispensing member comprises a second part, which is widened with respect to the protruding part, the protruding part extending radially with respect to the second part.

6. The storage device as claimed in claim 1, wherein the dispensing member has a front-to-rear cross section of substantially triangular shape along a longitudinal axis B-B of the dispensing member.

7. The storage device as claimed in claim 1, further comprising a cover configured to cooperate with the cartridge.

8. The storage device as claimed in claim 7, wherein the cover comprises an internal face configured to face toward the cartridge, the internal face comprising at least one retaining rib extending longitudinally over the internal face and configured to be arranged at least partially in the cavity when the cover cooperates with the cartridge.

9. An assembly comprising:
   a storage device comprising:
      a cartridge comprising a cavity, the cavity comprising:
         a bottom;
         a first portion shaped in order to receive strips;
         a second portion that is deeper than the first portion with respect to an axis D-D substantially perpendicular to the bottom of the cavity; and
         an inclined intermediate portion connecting the first portion and the second portion;
      a dispensing member configured to cooperate with the cartridge, the dispensing member being at least partially accommodated in the second portion, the dispensing member comprising:
         a protruding part having a contact surface shaped in order to cover at least a first end of each of the strips, the contact surface facing toward the bottom of the cavity of the cartridge and overhanging the inclined intermediate portion,
      wherein the dispensing member is configured to be mobile in rotation between:
         a resting position, in which the protruding part extends at a distance from the inclined intermediate portion, and
         an operating position, in which the protruding part converges toward the inclined intermediate portion so as to press the first end of each of the strips against the inclined intermediate portion; and
      at least one analysis strip accommodated in the first part of the cavity of the storage device, positioned flat with respect to the bottom of the cavity, along the longitudinal axis of the storage device.

10. The assembly as claimed in claim 9, wherein in the resting position of the dispensing member, the first end of each strip rests under the contact surface of the protruding part of the dispensing member.

11. The assembly as claimed in claim 9, wherein in the operating position of the dispensing member, the first end of each of the strips is pressed against the inclined intermediate portion, and is pinched between the protruding part of the dispensing member and the inclined intermediate portion.

* * * * *